United States Patent [19]

Pyle

[11] 3,998,592

[45] Dec. 21, 1976

[54] THERMOELECTRIC HEAT PUMP FOR CHEMILUMINESCENCE DETECTORS

[75] Inventor: William I. Pyle, Costa Mesa, Calif.

[73] Assignee: Ford Motor Company, Dearborn, Mich.

[22] Filed: Dec. 24, 1975

[21] Appl. No.: 644,224

[52] U.S. Cl. .......................... 23/254 E; 250/361 C
[51] Int. Cl.² ....................................... G01N 21/26
[58] Field of Search ......... 23/254 E, 254 R, 232 E, 23/232 R; 250/361 C

[56] References Cited

UNITED STATES PATENTS

| | | | |
|---|---|---|---|
| 3,025,745 | 3/1962 | Liston | 23/232 E X |
| 3,528,779 | 9/1970 | Fontijn | 23/232 E |
| 3,710,107 | 1/1973 | Warren et al. | 23/232 R UX |
| 3,734,691 | 5/1973 | Kukla et al. | 23/254 R X |
| 3,882,028 | 5/1975 | Zolner | 23/254 E X |
| 3,888,630 | 6/1975 | Hoeg | 23/254 E X |
| R28,374 | 3/1975 | Colvin et al. | 23/254 R |
| R28,376 | 3/1975 | Warnick et al. | 23/232 R |

Primary Examiner—Robert M. Reese
Attorney, Agent, or Firm—Robert A. Benziger; Keith L. Zerschling

[57] ABSTRACT

A chemiluminescence detector is comprised of a gaseous reaction chamber having a light transmitting element mounted to define one wall of the reaction space. A light responsive device, for example a photomultiplier, is arranged to receive light generated by a chemiluminescent reaction within the reaction chamber and transmitted through the light transmitting element. A thermoelectric heat pump means is situated in proximity to the reaction chamber and to the photomultiplier. The heat pump means is arranged to provide for cooling of the photomultiplier by extracting heat therefrom while simultaneously heating the reaction chamber. The thermoelectric heat pump is comprised of at least one mounting gasket means arranged to have a first surface in contact with the housing of the reaction chamber and a second surface in contact with a portion of the housing of the light sensing means. The thermoelectric heat pump includes a plurality of electrically serially connected thermoelectric coolers embedded within the gasket means and arranged to have one surface of each in thermal contact with the light sensing means and the opposite surface of each in contact with the reaction chamber housing. The thermoelectric coolers are arranged to extract thermal energy (heat) from the housing of the light sensing element, thereby lowering its temperature, and to apply this thermal energy to the housing of the reaction chamber thereby elevating its temperature and promoting the chemiluminescent reaction.

3 Claims, 5 Drawing Figures

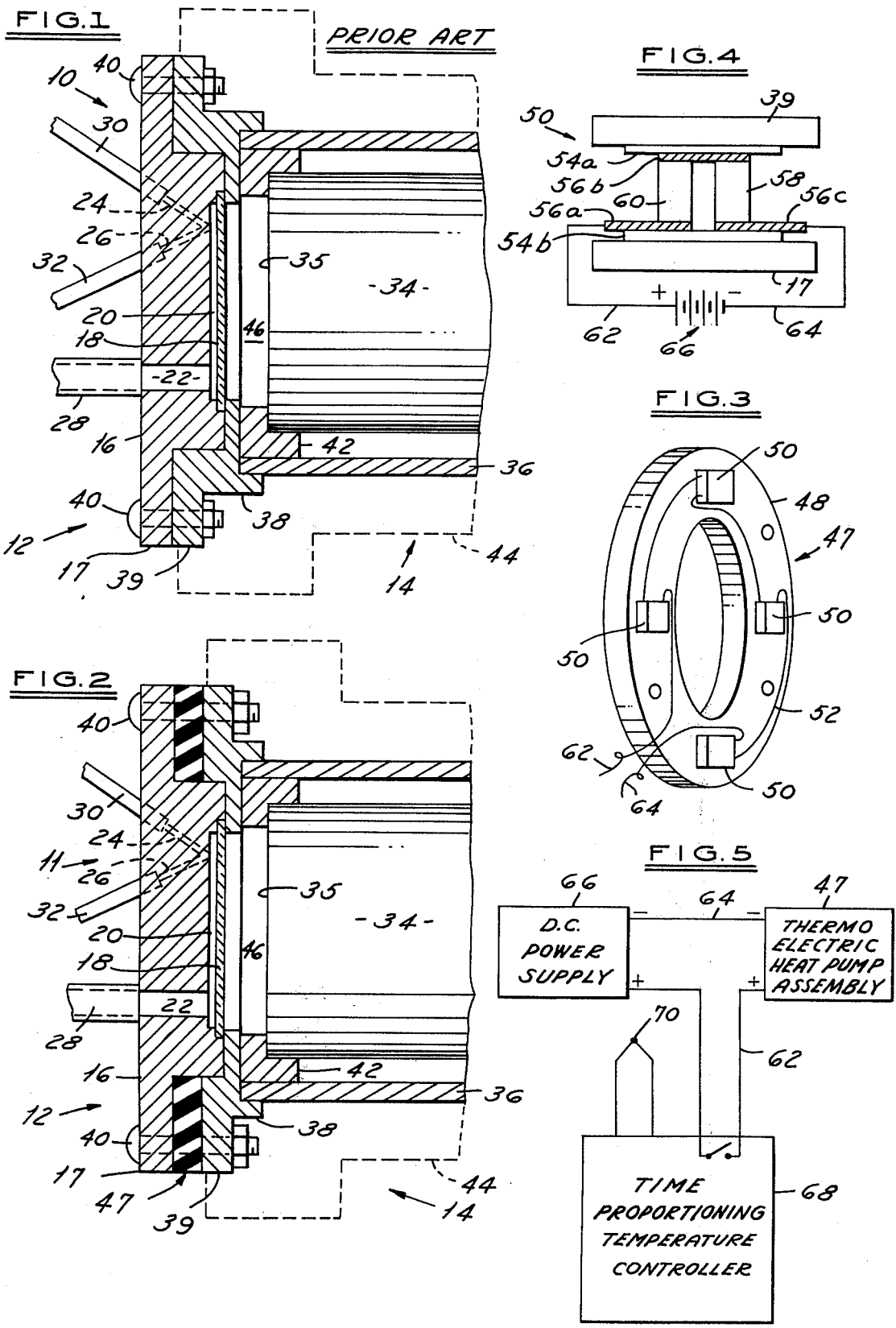

THERMOELECTRIC HEAT PUMP FOR CHEMILUMINESCENCE DETECTORS

BACKGROUND OF THE INVENTION

1. Field of the Invention

The present invention is directed to the field of chemiluminescence analyzers. More particularly still, the present invention is directed to that portion of the abovenoted field which is concerned with improving the electrical signal response and sensitivity of a chemiluminescence detector. More particularly still, the present invention is concerned with a technique and apparatus for improving the electrical operation of a light sensing device used to sense illumination produced by a chemiluminescent reaction while simultaneously and concomitently improving the conditions of the reaction to thereby promote the chemiluminescence producing reaction.

2. Description of the Prior Art

The U.S. Pat. Nos. RE 28,374 and RE 28,376 in the names of Colvin et al. and Warnick et al. respectively, describe a Chemiluminescent Instrument and Chemiluminescent Process, respectively. It has been determined that the electrical output signal produced by a chemiluminescence detecting and/or analyzing instrument, as generally described in the aforenoted reissue patents, can be improved if the signal-to-noise ratio of the electrical light sensing means be increased. The light sensing means is typically a photomultiplier. While photomultipliers are known having large signal-to-noise ratios, they are very expensive. In order to use the less expensive light sensing means, it has been the practice to reduce the temperature of the light sensing element, and particularly the cathode of the photomultiplier used as the light sensing element. Accordingly, it has been the prior art practice to provide thermal insulation for the photomultiplier reaction chamber assembly to insulate that assembly from ambient temperature and to further provide cooling for the assembly. One form of assembly cooling has been a thermoelectric heat pump. According to the prior art, the heat extracted from the assembly is rejected to the ambient environment. This approach has successfully reduced the operating temperature of the light sensing means. However, the lowering of the temperature of the light sensing means has required that the viewing window of the reaction chamber be thickened. This has been necessitated to prevent detrimental reduction of the temperature of the reaction chamber. It has also resulted in a decrease of the light energy received by the light sensing means.

A further problem which has been encountered in the prior art is the occurrence of vapor condensation within the reaction chamber and particularly on the viewing window. This problem is a result of the dew point of the sample gas being very close to normal ambient room temperature. This problem has been aggravated by the cooling of the photomultiplier and reaction chamber assembly below the ambient temperature.

I have determined that the quantity of light generated within the chemiluminescent reaction chamber portion of such an assembly is less than one would expect under identical gas flow conditions with apparatus which does not cool the reaction chamber/photomultiplier assembly. It is therefore an object of the present invention to provide an improved cooling apparatus for cooling the light sensing element of a chemiluminescence detection instrument which does not adversely affect the generation of light in the chemiluminescent reaction chamber. It is a further object of the present invention to provide a method and apparatus for cooling the light sensing element in a chemiluminescence detection instrument which does not cause a lowering of the temperature of the chemiluminescent reaction chamber. It is a still further, and a particular, object of the present invention to provide a method and apparatus for cooling the light sensing element of a chemiluminescence instrument which will permit the chemiluminescent reaction chamber to be operated at a temperature which is higher than the temperature of the light sensing element. More particularly still, it is a principal object of the present invention to provide a method and apparatus for cooling the light sensing element of the chemiluminescence detection instrument while providing simultaneous heating of the chemiluminescent reaction chamber.

SUMMARY OF THE INVENTION

The present invention provides a chemiluminescence detection instrument with a thermoelectric heat pump situated between the light sensing element and the reaction chamber and arranged to extract heat energy from the light sensing element and to apply this rejected heat to the housing of the chemiluminescent reaction chamber. According to the present invention, the thermoelectric heat pump is comprised of a plurality of electrically serially connected Peltier effect devices, hereinafter referred to as thermoelectric coolers, having a heated surface and a cooled surface embedded within an insulating gasket means. The heat pump gasket means is arranged in sealing relationship around the viewing window of the reaction chamber intermediate the reaction chamber and the light sensing means. The thermoelectric heat pump is oriented so that the cooled surface of each of the thermoelectric coolers is in heat exchange contact with the housing of the light sensing means and the heated surface of each of the thermoelectric coolers is in heat exchange contact with the housing of the chemiluminescent reaction chamber.

According to one aspect of the present invention, the thermoelectric coolers may be provided with a controlled source of electrical energy responsive to a sensed temperature. This sensed temperature may be either the temperature of the light sensing means or the temperature of the chemiluminescent reaction chamber. Alternatively, the thermoelectric coolers may be constantly energized by a DC power supply with the temperatures of the chemiluminescent reaction chamber and the light sensing means being allowed to stabilize without the application of any control to the thermoelectric coolers.

BRIEF DESCRIPTION OF THE DRAWINGS

FIG. 1 illustrates a fragmentary sectional view of a chemiluminescence detection instrument according to the prior art.

FIG. 2 illustrates a chemiluminescence detection instrument according to the present invention in a fragmentary sectional view similar to the view of FIG. 1.

FIG. 3 illustrates the thermoelectric heat pump of the present invention.

FIG. 4 illustrates a typical Peltier effect apparatus and its operation.

FIG. 5 illustrates a block diagram schematic circuit illustrating one form of temperature control for the present invention

DETAILED DESCRIPTION OF THE PREFERRED EMBODIMENT

Referring now to the drawing wherein like numerals designate like structure throughout the various views thereof, FIG. 1 illustrates a fragmentary sectional view of a chemiluminescence detection instrument 10 according to the prior art. Chemiluminescence detection instrument 10 is comprised of a chemiluminescent reaction chamber portion 12 and a light sensing instrument portion 14. Chemiluminescent reaction chamber portion 12 is comprised of a ported reaction chamber housing body 16 and viewing window 18. Housing body 16 is provided with an extending flange 17. The reaction chamber housing body 16 and the viewing window 18 are cooperative to define a reaction space 20. Reaction chamber housing body 16 is provided with gas flow ports 22, 24, and 26. Gas flow port 22 communicates with an exhaust conduit 28. Gas flow port 24 communicates with a first reactant flow conduit 30. Gas flow port 26 communicates with second reactant conduit 32. Exhaust conduit 28 may communicate, for example, with a gas pump so that gas may be exhausted from reaction space 20 through exhaust conduit 28. Reactant conduits 30, 32 may be communicated to separate sources of gases which, upon mixing in the reaction space 20, will react to produce chemiluminescence. By way of example, conudit 30 may communicate with an internal combustion exhaust system wherein the exhaust gas is known to include oxides of nitrogen. Conduit 32 may communicate to a gas source including a known quantity ozone. It is known that ozone and oxides of nitrogen react to produce chemiluminescence.

Light sensing instrument portion 14 is comprised of a light sensing instrument 34 which may be, for example, a photomultiplier. Light sensing instrument 34 is operative to receive light energy generated within reaction space 20 by a chemiluminescent reaction and transmitted through viewing window 18. Upon receipt of incident light energy, instrument 34 is operative to generate an electrical signal having an electrical characteristic directly related to the quantity of light, in this instance chemiluminescence, sensed by light sensing instrument 34. Light sensing instrument 34 is received and supported within housing portion 36. Housing portion 36 may be connected to support means 38 by any convenient means. Support means 38 includes a flange 39 which may be coupled to reaction chamber housing body 16 by any convenient means such as, for example, mounting bolts 40 extending through flanges 17 and 39.

It is frequently convenient to fabricate a chemiluminescence detection instrument 10 so that component parts such as viewing window 18 are circular. This is a result of the fact that light sensing instrument 34 is generally of a circular configuration. In order to properly support light sensing instrument 34 and to maintain a relatively fixed position between the viewing window 18 and the light receiving end portion 35 of light sensing means 34, a generally annular support collar 42 is illustrated. Since light sensing means 34 is frequently a photomultiplier, it has become the standard practice to insulate light sensing instrument portions 14 and such insulation is here illustrated by phantom line portion 44. In order to maintain the light sensing instrument at a relatively low temperature (in order to maintain a desired high signal-to-noise ratio) it is frequently the practice that light sensing instrument 34 will be cooled by means not here illustrated. Since the chemiluminescent reaction is normally carried forward at a temperature in excess of the temperature to which light sensing element 34 may be cooled, the void 46 between the viewing window 18 and the light receiving surface 35 of the light sensing instrument 34 is usually filled with a dry gas to prevent vapor condensation from occurring to lower the level of light energy received by surface 35 of light sensing instrument 34.

In the operation of a chemiluminescence detection instrument as illustrated in FIG. 1, a sample gas which may be, or may contain as a component, a gas to be tested will be provided through one of the two reactant conduits 30, 32, for example through conduit 30 and a selected reactant will be provided through the other of the reactant conduits 30, 32, for example conduit 32. These two gases will be mixed as they enter the reaction space 20 and, upon mixing, will generate chemiluminescence as a function of the quantity of gas to be detected and measured which may be present in the gas sample. The gas flows will be exhausted continuously from reaction space 20 through the gas flow port 22 and exhaust conduit 28.

Referring now to FIG. 2, the improved chemiluminescence detection instrument 11 according to the instant invention is illustrated in a fragmentary sectional view comparable to the view of FIG. 1. The chemiluminescence detection instrument of FIG. 2 is comprised of a chemiluminescent reaction chamber portion 12 and a light sensing instrument portion 14. The chemiluminescent reaction chamber portion 12 is comprised of a ported reaction chamber housing body 16 and a viewing window 18. Housing 16 is similarly provided with a radially extending flange portion 17. The reaction chamber housing body 16 and the viewing window 18 are arranged to be cooperative to define a reaction space 20. Reaction chamber housing body 16 includes gas flow ports 22, 24, 26. Gas flow port 22 is communicated to an exhaust conduit 28. Gas flow ports 22, 24 are connected respectively to first and second reactant flow conduits 30, 32.

The light sensing instrument portion 14 of the chemiluminescence detection instrument 11 according to the present invention is comprised of a light sensing instrument 34 received within a housing portion 36. Housing portion 36 is coupled to support means 38. Support means 38 also is provided with a radially extending flange 39. Support means 38 are mounted to the reaction chamber housing body 12 by means of mounting bolts 40 which extend through extending flanges 17, 39 of the reaction chamber housing body 16 and the support means 38, respectively. Annular support collar 42 is received within housing portion 36 and supports light sensing instrument 34 in proper position with respect to the viewing window 18 so that chemiluminescence may be incident upon light receiving surface 35. Insulation means 44 are illustrated to be in a generally surrounding relationship with respect to the housing portion 36 in order to provide a temperature barrier between the ambient and the light sensing instrument 34.

According to the present invention, and with reference to FIGS. 2 and 3, the thermoelectric heat pump 47 is illustrated to be intermediate the flanges 17, 39 of the housing body 16 and the support means 38, respectively. Thermoelectric heat pump 47 is comprised of a generally annular collar or gasket 48. Gasket 48 preferably is formed of a suitable gas tight material having a relatively low thermal coefficient such that gasket 48 may act as a thermal barrier between the flange 39 of support means 38 and the flange 17 of housing body 16. Such a material may be, for example, a silicon-rubber gasket material. Thermoelectric heat pump 47 is further comprised of a plurality of thermoelectric coolers 50. Thermoelectric coolers 50 are embedded within gasket 48 and are substantially equidistantly positioned around gasket means 48. As is more fully described hereinbelow with reference to FIG. 4, the thermoelectric coolers 50 have a pair of generally parallel planer surfaces which, upon the application of a voltage, assume a temperature differential. The planer surfaces are recessed slightly with respect to the surfaces of gasket 48. As illustrated in FIG. 3, the plurality of thermoelectric coolers includes in this instance four such devices. The thermoelectric coolers 50 are connected in an electrical series relationship with respect to each other by suitable electrical conductors here illustrated as number 52. The electrical conductors 52 are typically insulated copper or aluminum wire and may be embedded within gasket means 48 or may be situated within grooves provided therefor along a surface of gasket means 48.

Referring now to FIG. 4, a typical thermoelectric cooler 50 is illustrated. Thermoelectric cooler 50 is comprised of a pair of generally planer, parallel outer plate members 54a, 54b which are selected of a material which exhibits good thermal conductivity while being at the same time an electrical insulator. A ceramic-metal laminate usually provides adequate electrical insulation and thermal conductivity to be used as plates 54. As illustrated in this figure, the outer surface of the plate member 54 is in thermal energy exchange contact with a surface of flange 39. The oppositely disposed surface of plate member 54b is in thermal energy exchange contact with the flange 17. A plurality of generally planer, electrically conductive and thermally conductive plates 56 are situated in intimate thermal contact with each of the outer plate member 54 as for example at 56. As here illustrated, one of the outer plates 54a is in intimate thermal exchange contact with one of the conductor plates 56b while the other of the outer plates 54b is in intimate thermal contact with a pair of spatially separated plates 56a and 56c. As thus described, conductor plates 56a and 56c may be considered to be the electrodes or terminals for the thermoelectric cooler 50. The plate 56 in contact with the outer plate 54a is electrically communicated to the conductor plates 56a and 56c (the conductor plates in contact with the outer plate 54b) are a plurality of first and second semiconductor material members here shown as members 58, 60.

The semiconductor material members 58, 60, are selected to have dissimilar characteristics and are arranged so that a series circuit from conductor plate 56a to conductor plate 56c may be established through conductor plate 56b. As thus described, semiconductor material members 58, 60 are connected electrically in series and thermally in parallel so that two thermal junctions are established at outer plate members 54a and 54b. The spatial separation assures that conductor plates 56a and 56c will not be in intimate electrical contact. The semiconductor material members 58, 60 are selected so that the semiconductor material 58 may be, for example, P-type semiconductor material and semiconductor 60 may be N-type semiconductor material. As is understood, N-type semiconductor material has more electrons than are necessary to complete a perfect molecular lattice structure and P-type semiconductor material has a deficiency in the number of electrons necessary to complete a perfect molecular lattice structure.

Upon the application of electrical energy to the pair of electrodes 56a, 56c, an electrical current will flow through the thermoelectric cooler 50 and the flow of electrons and holes (electron deficiencies) will cause heat energy to be absorbed through outer plate 54a, hereafter also referred to as the "cold junction" and to be carried to the outer plate 54b, hereafter also referred to as the "hot junction", establishing a temperature differential between outer plate members 54a, 54b.

As illustrated in this FIG. 4, and as would be applicable to the thermoelectric heat pump of FIG. 3, the connection of electode 56a to the positive voltage terminal of a DC voltage source 66 as by conductor 62 and the connection of electrode 56c to the negative voltage terminal of a DC voltage source 66 as by conductor 64 will establish an electric current flow through the thermoelectric cooler 50. In this figure, source 66 is shown as a battery. As will become apparent from the discussion which follows, source 66 could also be a regulated or unregulated voltage source. According to the present invention, and with reference to FIGS. 2, 3 and 4, the thermoelectric coolers 50 are situated within gasket means 48 to place the cold junction of each cooler 50 in heat exchange contact with the flange 39 of support means 38 while placing the hot junction of each cooler 50 in thermal exchange contact with the flange 17 of reaction chamber housing body 16. Upon the application of electrical energy to the electrical circuit input leads 62, 64 an electrical circuit will be established through each of the thermoelectric coolers 50. This circuit and subsequent electrical current flow will cause heat to be absorbed by the cold junction 54a from flange 39 and to be transported to, and dissipated by thermal rejection at, the hot junction 54b and flange 17. The temperature of support means 38, housing portion 36 and, most importantly, light sensing means 34 will thereby be lowered. As is known in this art, the lowering of the temperature of the light sensing means 34 will produce an improvement in the signal-to-noise ratio of such an instrument. According to the present invention, the heat extracted from light sensing means 34 will be rejected into the flange 17 of reaction chamber housing body 16 causing the temperature of reaction chamber housing body 16 to be elevated above the ambient temperature. Thus, while the thermoelectric coolers 50 are operating to lower the temperature of light sensing instrument 34 below the ambient temperature and the insulation means 44 are operative to assist in reducing the heat transference to light sensing instrument 34 from the ambient, the rejection of heat from thermoelectric coolers 50 will cause the temperature of reaction chamber housing body 16 to be elevated above the ambient temperature. By elevating the temperature of the housing body 16, the chemiluminescence producing reaction within reaction space 20 will be promoted and enhanced. The establishment of a temperature differential between the light receiving surface 35 of light sensing instrument 34 and the viewing window 18 could cause vapor to condense on the light receiving surface 35. In order to prevent this from occurring, the space or void 46 is filled with a dry gas and is thereafter sealed. In order to conveniently establish the seal, gasket means 48 is selected to be relatively impervious to the dry gas. The axial dimension of gasket means 48, that is the dimension of gasket 48 in the direction of the axis of the chemiluminescence detection instrument 11 is selected to be slightly greater than the thickness of the thermoelectric coolers 50. This permits a small degree of compression of gasket means 48 upon assembly to assure sealing of void 46.

In one form of the instant invention, electric energy is provided to electrical leads 62, 64 from a regulated DC source. This establishes a relatively constant level of electrical current through the electrical circuit including the thermoelectric coolers 50. In such an embodiment, the end operating (cooled) temperature of the light sensing instrument 34 and the end operating (heated) temperature of the reaction space 20 will stabilize to temperatures which will be determined as a function of the ambient temperature and of the physical size and geometry of the chemiluminescence detection instrument 11. In the event that it is desired to maintain either the light sensing instrument 34 or the reaction space 20 at a predetermined constant temperature, a control circuit may be used to modulate the application of electrical energy to the thermoelectric heat pump 47.

The presently preferred thermoelectric coolers 50 are available from Borg-Warner Corporation and are identified by module model number 930-17. These thermoelectric coolers are capable of maintaining temperature differential between the cold junction and the hot junction of about sixty centigrade degrees (60° C). It will be appreciated that selection of a specific thermoelectric cooler will be determined as a function of the temperature differential desired, the amount of heat to be pumped from the cold junction to the hot junction and the geometry of the reaction chamber housing and the light sensing instrument housing.

Referring now to FIG. 5, one form of such a circuit is illustrated in a block diagram schematic. According to FIG. 5, the thermoelectric heat pump 47 is connected by one electrical lead directly to a dc power supply 66. The other electrical lead 62 of the thermoelectric heat pump 47 is connected to a time proportioning temperature control means 68 which operates to make or break the electrical circuit from electrical lead 62 to the other terminal of the dc power supply 66. The time proportioning of controller 68 may be controlled, for example, by the use of thermocouple 70. Thermocouple 70 may be situated in thermal contact with a suitable component of either the chemiluminescent reaction portion 12 or the light sensing instrument portion 14 to provide a representative temperature signal to the time proportioning temperature control means 68.

It will be readily appreciated that the present invention accomplishes its stated objectives. By situating a thermoelectric heat pump 47 in heat exchange relation to, and intermediate, the chemiluminescent reaction chamber portion 12 and the light sensing instrument portion 14 of a chemiluminescence detection instrument, the temperature of the light sensing portion may be reduced below ambient temperature to improve its signal-to-noise ratio while simultaneously taking the heat extracted from the light sensing instrument portion 14 and applying this heat to the chemiluminescent reaction chamber portion 12 of such a detection instrument in order to maintain the temperature of the chemiluminescent reaction chamber portion 12 elevated with respect to the ambient temperature. By elevating the reaction chamber temperature, the chemiluminescent reaction is enhanced and the temperature of the sample gas may be maintained above the dew point. Thus, the signal-to-noise ratio of the light sensing instrument may be improved while simultaneously improving the conditions, i.e., increasing the temperature, under which the chemiluminescence producing reaction is being carried forward.

I claim:
1. In a chemiluminescence detection instrument of the type having a reaction chamber housing body and a viewing window cooperative therewith to define a reaction space and a light sensing instrument portion including a light sensing instrument positioned to receive any chemiluminescence produced in the reaction space and transmitted through the viewing window, the improvement comprising:
   thermoelectric heat pump means having at least one cooled surface and at least one heated surface situated intermediate the reaction chamber housing body and the light sensing instrument portion and having said cooled surface in thermal energy exchange contact with the light sensing instrument portion and said heated surface in thermal energy exchange contact with the reaction chamber housing body.

2. The improved chemiluminescence detection instrument according to claim 1 wherein said thermoelectric heat pump means is comprised of a plurality of thermoelectric coolers, each of which has a heated surface and a cooled surface, connected in electrical series relation.

3. The improved chemiluminescence detection instrument according to claim 2 wherein said thermoelectric coolers and associated electrical interconnections are embedded within means defining an annular gasket.

* * * * *